(12) United States Patent
Prasad et al.

(10) Patent No.: US 11,080,849 B2
(45) Date of Patent: Aug. 3, 2021

(54) SYSTEMS AND METHODS FOR DEEP LEARNING BASED AUTOMATED SPINE REGISTRATION AND LABEL PROPAGATION

(71) Applicant: General Electric Company, Schenectady, NY (US)

(72) Inventors: Raghu Prasad, Bangalore (IN); Jignesh Dholakia, Bangalore (IN); Kavitha Manickam, Bangalore (IN)

(73) Assignee: General Electric Company, Schenectady, NY (US)

( * ) Notice: Subject to any disclaimer, the term of this patent is extended or adjusted under 35 U.S.C. 154(b) by 100 days.

(21) Appl. No.: 16/231,261

(22) Filed: Dec. 21, 2018

(65) Prior Publication Data

US 2020/0202515 A1   Jun. 25, 2020

(51) Int. Cl.
G16H 50/20 (2018.01)
G06T 7/00 (2017.01)
G06N 3/08 (2006.01)
G06T 11/00 (2006.01)
G16H 30/40 (2018.01)

(52) U.S. Cl.
CPC ............. *G06T 7/0012* (2013.01); *G06N 3/08* (2013.01); *G06T 11/003* (2013.01); *G16H 30/40* (2018.01); *G06T 2207/10072* (2013.01); *G06T 2207/20084* (2013.01)

(58) Field of Classification Search
CPC combination set(s) only.
See application file for complete search history.

(56) References Cited

U.S. PATENT DOCUMENTS

| | | | |
|---|---|---|---|
| 6,128,398 A * | 10/2000 | Kuperstein | G06K 9/00288 382/118 |
| 6,856,826 B2 | 2/2005 | Seeley et al. | |
| 7,095,881 B2 | 8/2006 | Lelong et al. | |
| 7,945,117 B2 | 5/2011 | Hermosillo Valadez et al. | |
| 8,014,575 B2 * | 9/2011 | Weiss | B60R 25/00 382/128 |
| 8,600,131 B2 | 12/2013 | Miller et al. | |
| 8,698,795 B2 | 4/2014 | Grewer et al. | |
| 9,427,286 B2 | 8/2016 | Siewerdsen et al. | |
| 10,176,388 B1 * | 1/2019 | Ghafarianzadeh | G06K 9/00671 |
| 10,242,665 B1 * | 3/2019 | Abeloe | G06N 3/0454 |
| 10,460,488 B2 * | 10/2019 | Bronkalla | G06T 11/60 |
| 10,499,857 B1 * | 12/2019 | Nguyen | G06N 3/08 |
| 10,537,277 B2 * | 1/2020 | Wu | A61B 5/04012 |
| 2011/0181701 A1 * | 7/2011 | Varslot | G01N 15/088 348/46 |
| 2012/0035463 A1 * | 2/2012 | Pekar | G16H 30/20 600/411 |

(Continued)

*Primary Examiner* — Cindy Trandai

(57) ABSTRACT

Methods and systems are provided for whole-body spine labeling. In one embodiment, a method comprises acquiring a non-functional image volume of a spine, acquiring a functional image volume of the spine, automatically labeling the non-functional image volume with spine labels, automatically correcting the geometric misalignments and registering the functional image volume, and propagating the spine labels to the functional image volume. In this way, the anatomical details of non-functional imaging volumes may be leveraged to improve clinical diagnoses based on functional imaging, such as diffusion weighted imaging (DWI).

18 Claims, 13 Drawing Sheets

(56) References Cited

U.S. PATENT DOCUMENTS

| | | | |
|---|---|---|---|
| 2012/0172700 A1* | 7/2012 | Krishnan | G16H 30/20 600/407 |
| 2014/0056501 A1* | 2/2014 | Du | G06T 7/11 382/131 |
| 2014/0226889 A1* | 8/2014 | Liu | G06T 7/174 382/131 |
| 2015/0086096 A1* | 3/2015 | Liu | G06T 7/11 382/131 |
| 2015/0178938 A1* | 6/2015 | Gorman, III | G06T 7/143 382/131 |
| 2015/0228070 A1* | 8/2015 | Birkbeck | G06T 7/10 382/131 |
| 2017/0215806 A1* | 8/2017 | Bae | A61B 5/117 |
| 2017/0231713 A1* | 8/2017 | Siewerdsen | A61B 5/4566 382/128 |
| 2017/0337682 A1* | 11/2017 | Liao | G06T 7/30 |
| 2018/0137335 A1* | 5/2018 | Kim | G06K 9/00604 |
| 2018/0166067 A1* | 6/2018 | Dimitriadis | G10L 25/78 |
| 2018/0174311 A1* | 6/2018 | Kluckner | G06K 9/6259 |
| 2018/0239428 A1* | 8/2018 | Maheriya | G06F 3/014 |
| 2018/0260951 A1* | 9/2018 | Yang | G06K 9/00718 |
| 2018/0260981 A1* | 9/2018 | Gholipour-Baboli | A61B 5/055 |
| 2018/0301213 A1* | 10/2018 | Zehavi | A61B 6/032 |
| 2018/0342053 A1* | 11/2018 | Balagurusamy | G06T 7/11 |
| 2019/0021677 A1* | 1/2019 | Grbic | G06K 9/6267 |
| 2019/0030371 A1* | 1/2019 | Han | G06N 3/08 |
| 2019/0103190 A1* | 4/2019 | Schmidt | G06T 19/20 |
| 2019/0114836 A1* | 4/2019 | Holzer | G06K 9/00369 |
| 2019/0254772 A1* | 8/2019 | Leung | G06T 7/0012 |
| 2019/0370957 A1* | 12/2019 | Manickam | G06T 7/0012 |
| 2020/0022758 A1* | 1/2020 | Shoham | A61B 5/1116 |
| 2020/0074239 A1* | 3/2020 | Park | G06K 9/6257 |
| 2020/0105028 A1* | 4/2020 | Gao | G06T 5/002 |
| 2020/0155236 A1* | 5/2020 | Chi | A61B 34/10 |

* cited by examiner

SYSTEMS AND METHODS FOR DEEP LEARNING BASED AUTOMATED SPINE REGISTRATION AND LABEL PROPAGATION

FIELD

Embodiments of the subject matter disclosed herein relate to magnetic resonance imaging (MRI), and more particularly, to labeling whole-body spine image volumes, registering functional whole-body spine image volumes to non-functional image volumes, and propagating labels from non-function image volumes to functional image volumes.

BACKGROUND

The spine is the most complex anatomical structure in the entire human body. It is made up of twenty-six irregular bones connected in such a way that flexible curved structure results. The vertebral column is about 70 centimeters long in an average adult and features seven major divisions. Seven vertebrae found in the neck region constitute the cervical vertebrae, the next twelve comprise the thoracic vertebrae, and the five vertebrae supporting the lower back are the lumbar vertebrae. The sacrum, which is inferior to these vertebrae, articulates with the hip bones of the pelvis. The tiny coccyx terminates the entire vertebral column. Intervertebral discs act as shock absorbers and allow the spine to extend. These are the thickest in the lumbar and cervical regions, enhancing the flexibility in these regions. The degeneration of intervertebral discs is a relatively common phenomenon, with aging due to wear and tear, and is the major cause of back pain. Degenerative lumbar spine disease includes spondylosis (arthritic) and degenerative disc disease of the lumbar spine with or without neuronal compression or spinal instability.

Magnetic resonance imaging (MRI) is a medical imaging modality that can create pictures of the inside of a human body without using x-rays or other ionizing radiation. MRI uses a superconducting magnet to create a strong, uniform, static magnetic field. When a human body, or part of a human body, is placed in the magnetic field, the nuclear spins associated with the hydrogen nuclei in tissue water become polarized, wherein the magnetic moments associated with these spins become preferentially aligned along the direction of the magnetic field, resulting in a small net tissue magnetization along that axis. MM systems also include gradient coils that produce smaller-amplitude, spatially-varying magnetic fields with orthogonal axes to spatially encode the MR signal by creating a signature resonance frequency at each location in the body. Radio frequency (RF) coils are then used to create pulses of RF energy at or near the resonance frequency of the hydrogen nuclei, which add energy to the nuclear spin system. As the nuclear spins relax back to their rest energy state, they release the absorbed energy in the form of an RF signal. This signal is detected by the MRI system and is transformed into an image using reconstruction algorithms. Whole-body MRI scans of a patient may be used to image the spine to aide in identifying and diagnosing abnormalities.

BRIEF DESCRIPTION

In one embodiment, a method comprises automatically labeling a non-functional whole-body image volume of a spine with spine labels, automatically registering a functional whole-body image volume of the spine to the non-functional whole-body image volume, and propagating the spine labels to the registered functional whole-body image volume. In this way, the anatomical details of non-functional imaging volumes may be leveraged to improve clinical diagnoses based on functional imaging, such as diffusion weighted imaging (DWI).

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The diagnosis of abnormalities situated around the spine in whole-body imaging scans is challenging. For accurate diagnosis, the spine appearance, shape, and geometry measurements might need to be viewed in all multiplanar reformatted views for abnormality detection. Therefore, proper localization, segmentation, and labeling in all multiplanar reformatted views (e.g., axial, coronal, sagittal, and oblique) would help improve diagnosis by a clinician. However, manual segmentation and labeling of the spine in axial whole-body exams is a challenging task and does not guarantee accuracy. For example, a clinician may find it difficult to identify the spine segments in whole-body anatomical scans riddled by artifacts, intensity inhomogeneity, abrupt non-uniform intensity changes, patient motion, and degenerative changes. Further, in degenerative spine disease, the associated intensity changes due to neuronal compression, and so it is highly challenging to identify and manually label the spine in axial whole-body scans.

Nevertheless, the clinician may be interested in knowing the spatial location of a lesion situated near the spine region in a diffusion weighted imaging (DWI) whole-body scan. DWI can detect early changes in the lesion/tissue with its diffusivity index. Thus, acute lesions and the lesion conspicuity can be identified better in DWI. However, anatomical information or details might not be very well captured in DWI. Although several methods for automatic labeling have been established in the past, they are not robust in handling image contrast (e.g., inhomogeneities, non-uniform intensities) or susceptibility-related artifacts. As such, these methods are unsuitable for functional MM like DWI.

The following description relates to various systems and methods for whole-body spine labeling. In particular, systems and methods for automatically labeling the spine in functional image volumes are provided. A method for automatically labeling the spine in a functional MR image volume, such as the method depicted in FIG. 1, includes acquiring both non-functional MR images and functional MR images of a spine, automatically labeling the non-functional MR images, stitching and registering the non-functional MR images and the functional MR images, and propagating the labels of the non-functional images to the functional images. As used herein, "non-functional MR image" refers to a static (e.g., fixed) MR image. For example, each non-functional MR image may be acquired at a single time point and may depict anatomical structures (e.g., features) of the spine. As used herein, "functional MR image" refers to a moving MR image that detects changes in blood flow. For example, the functional MR image may include a series of images obtained over a time period, which may be compared to a control image to depict changes in activity associated with changes in blood flow, such as due to neuronal function of the spine.

Figure 2:
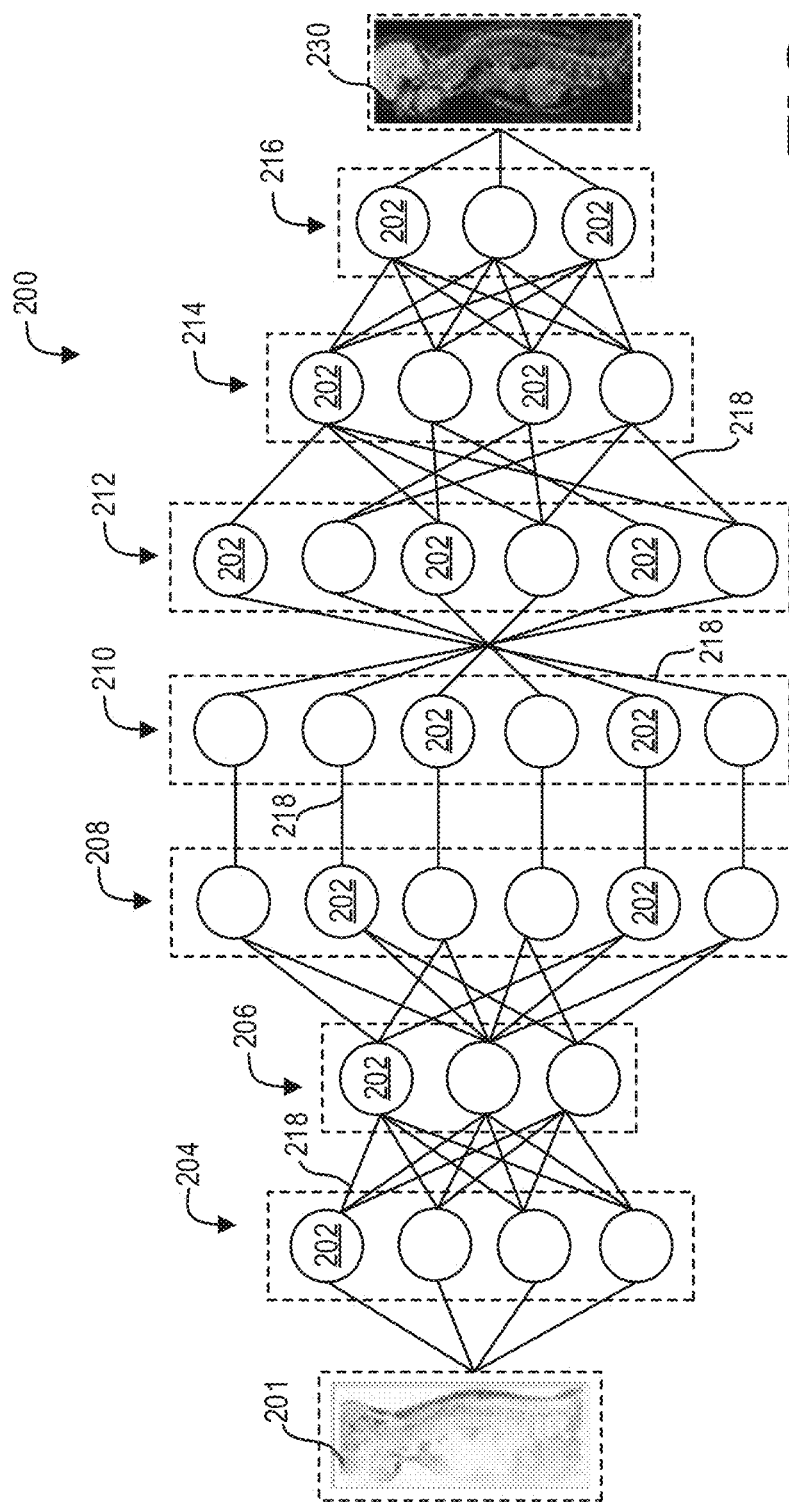
FIG. 2 shows a schematic diagram illustrating an example deep neural network according to an embodiment.
Figure 3:
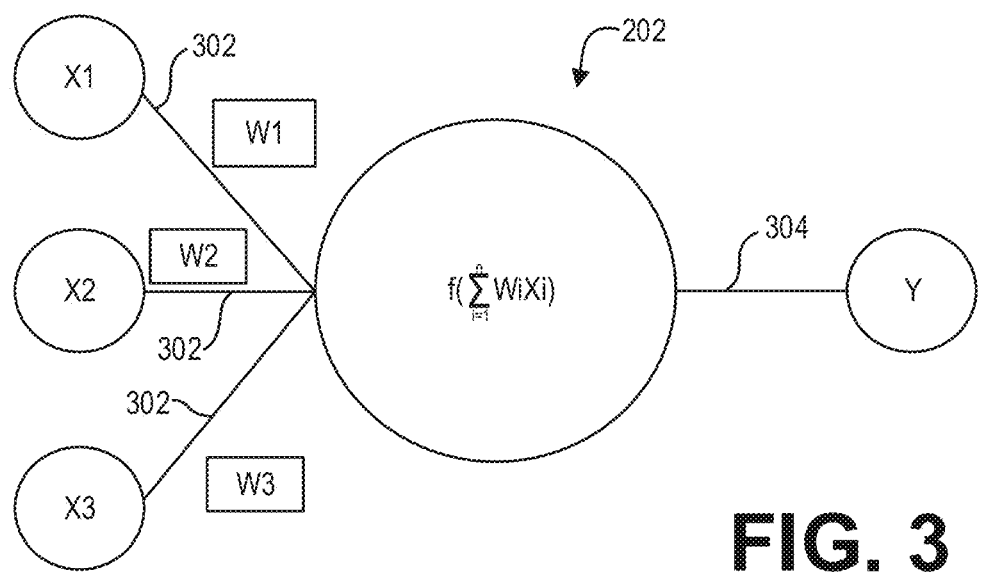
FIG. 3 shows a schematic diagram illustrating an example node of a deep neural network according to an embodiment.
Figure 4:
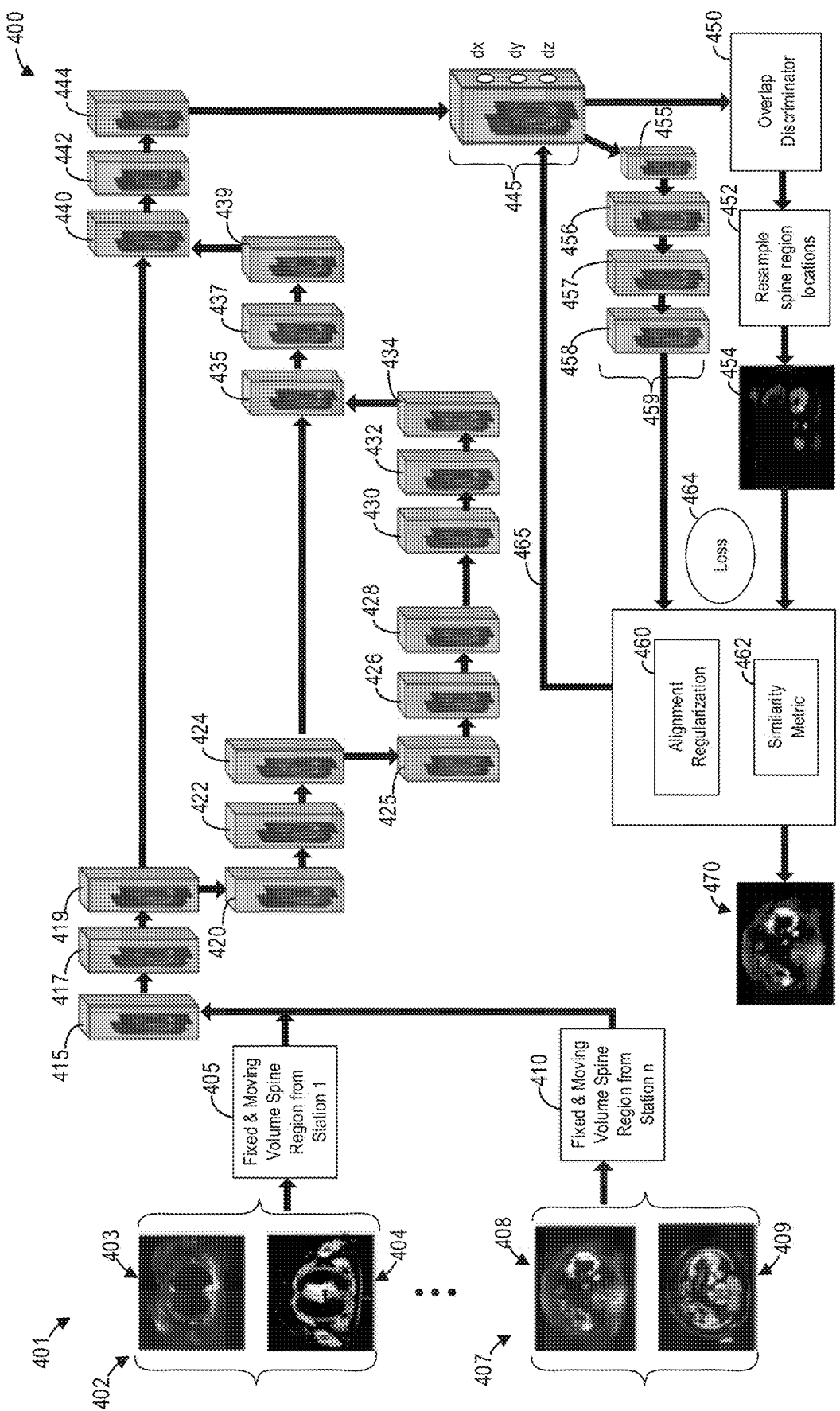
FIG. 4 shows a block diagram illustrating an example deep neural network for stitching and registering multi-station or single-station axial spine whole-body image volumes according to an embodiment.

Deep neural networks, such as the deep neural networks depicted in FIGS. 2 and 3, may be trained to perform the automatic labeling of the non-functional MR images, the automatic stitching and registering of the non-functional MR images and the functional MR images, and the automatic propagation of the labels. A deep neural network configured as depicted in FIG. 4 may automatically stitch non-functional MR images and functional MR images acquired at multiple stations into a single non-functional MR image volume and a single functional MR image volume, respectively, while simultaneously correcting for geometrical misalignments, as depicted by the example corrected whole spine image volume of FIG. 5.

Figure 6:
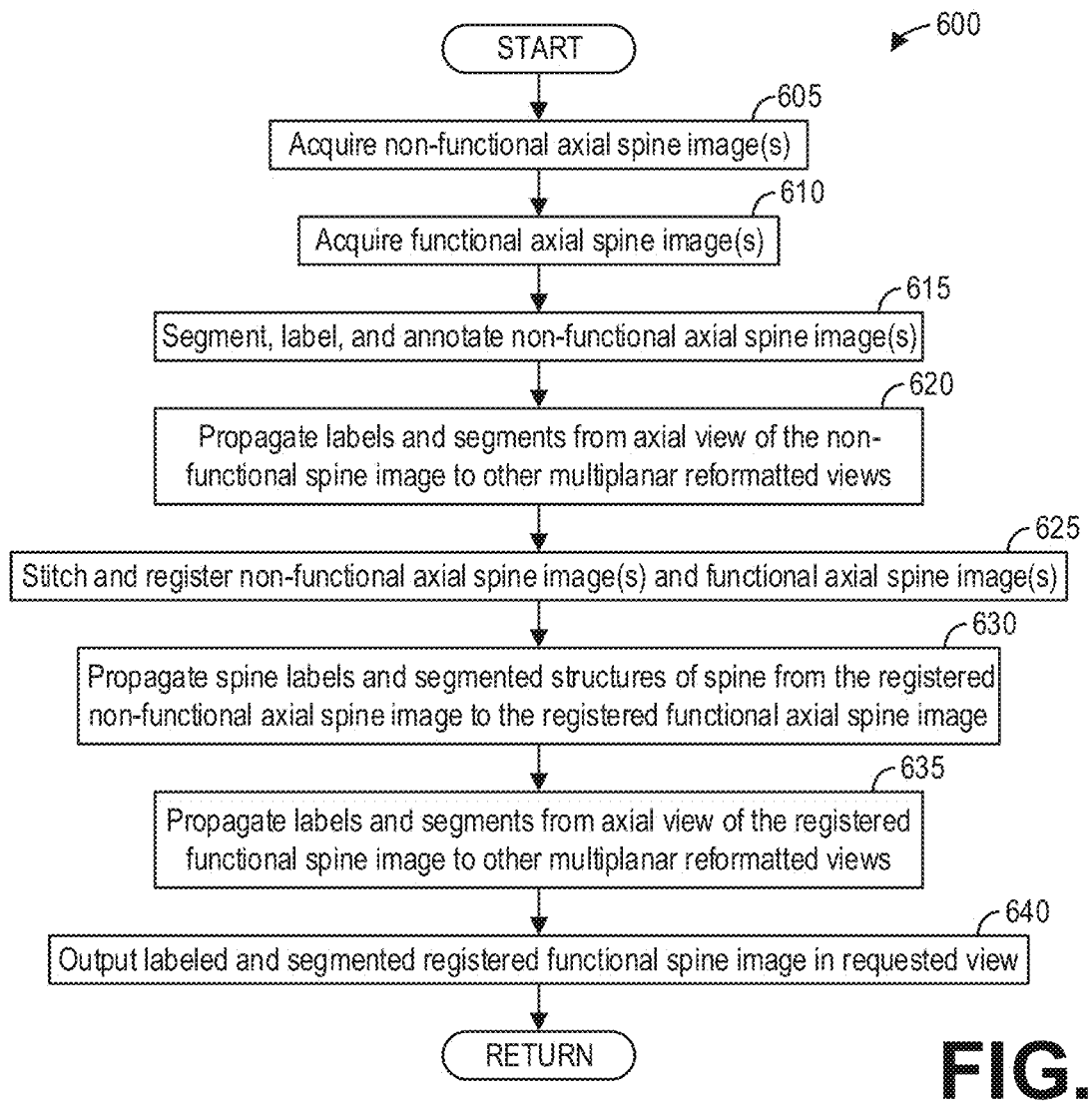
FIG. 6 shows a high-level flow chart illustrating an example method for labeling functional spine images according to an embodiment.
Figure 8:
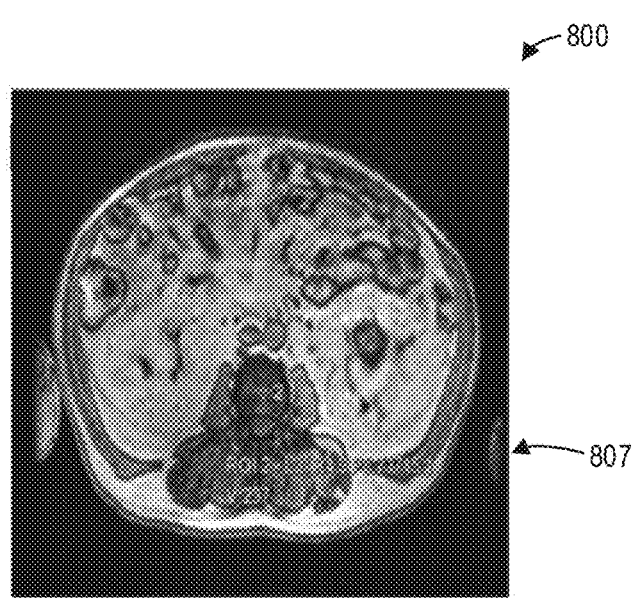
FIG. 8 shows an example of axial whole-body spine labeling by a deep neural network on a non-functional volume according to an embodiment.
Figure 9:
FIG. 9 shows a set of images depicting spine labeling propagated to various multi-planar reformatted views for a non-functional MR image volume according to an embodiment.
Figure 10:
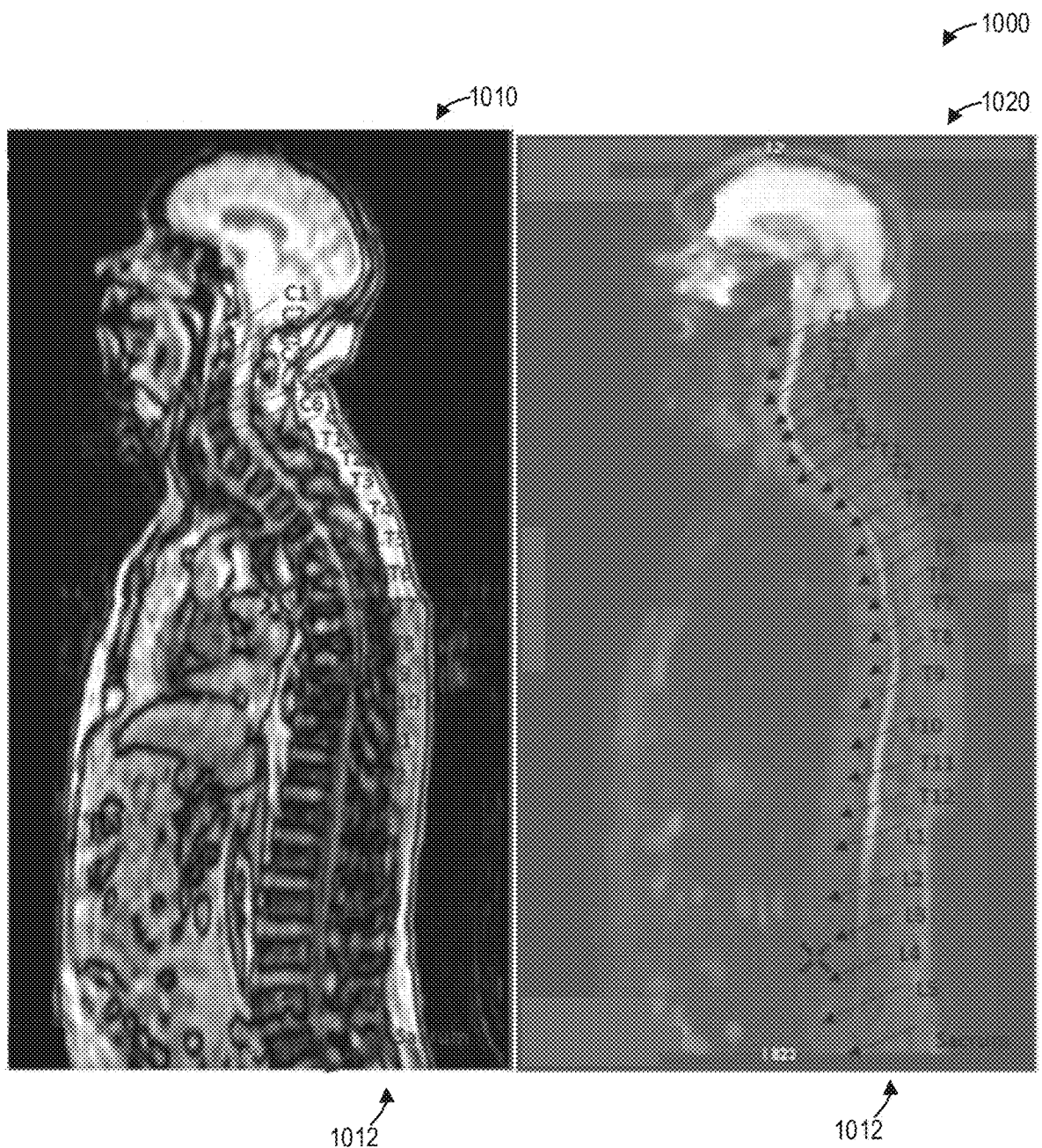
FIG. 10 shows a set of images depicting the propagation of labels and annotations of a spine from a non-functional volume to a functional volume according to an embodiment.

A method for automatically labeling functional image volumes, such as the method depicted in FIG. 6, may include outputting labeled and segmented registered functional spine images in one or more of the coronal, axial, oblique, and sagittal, views, as requested by a user. The non-functional MR images and the functional MR images, such as those depicted in FIG. 7, may be acquired via axial whole-body MR scans. The spine labeling of the axial non-functional MR images, depicted in FIG. 8, may be propagated to one or more of the multiplanar reformatted views, such as sagittal, coronal, and oblique, from the axial view, as depicted in FIG. 9. Furthermore, after registering the functional MR images to the non-functional MR images, the spine labeling from the non-functional MR images may be propagated to the functional MR images, as depicted in FIG. 10.

Figure 12:
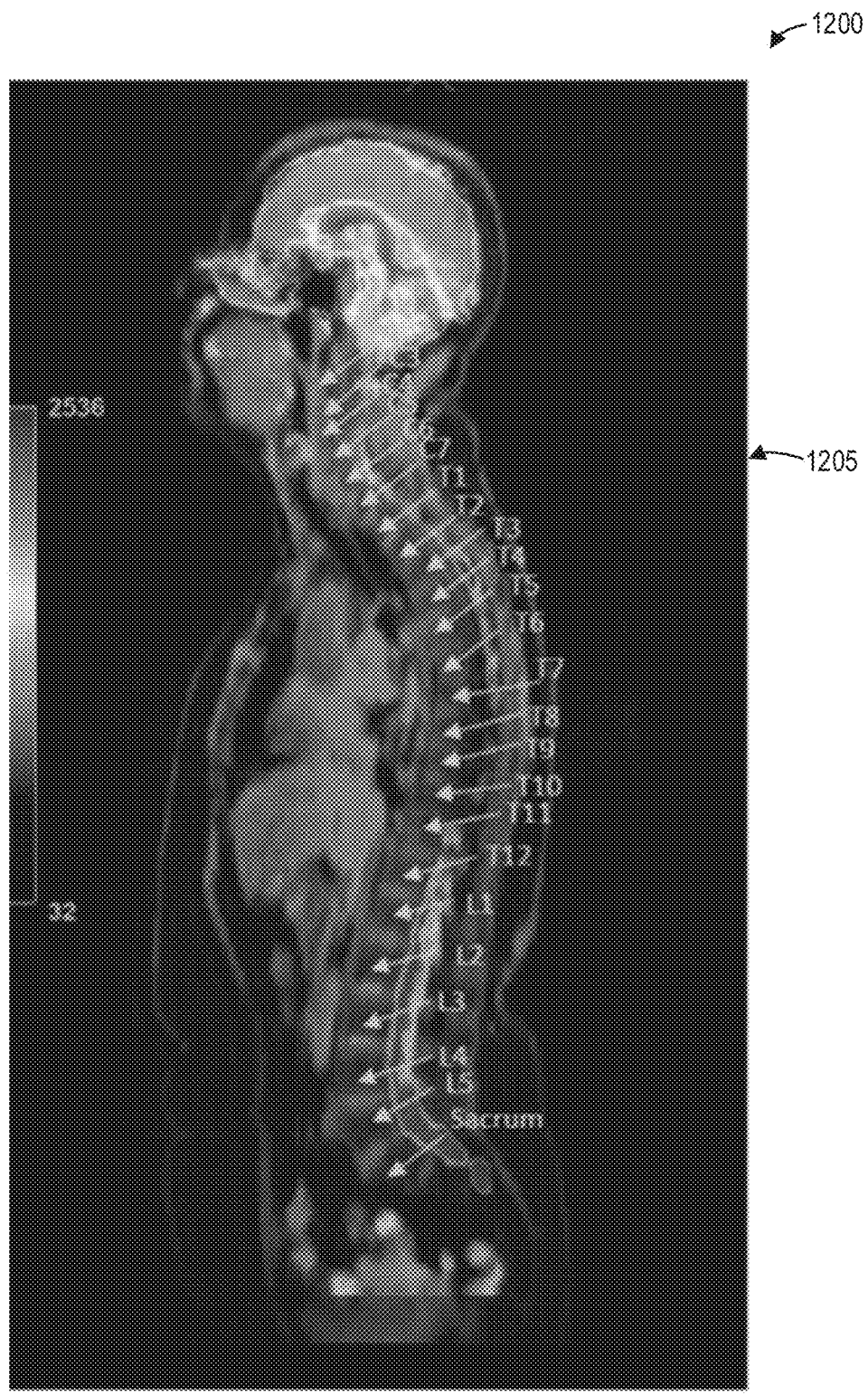
FIG. 12 shows an image depicting a fusion of non-functional and functional MR whole body anatomical data with spine labeling according to an embodiment.
Figure 14:
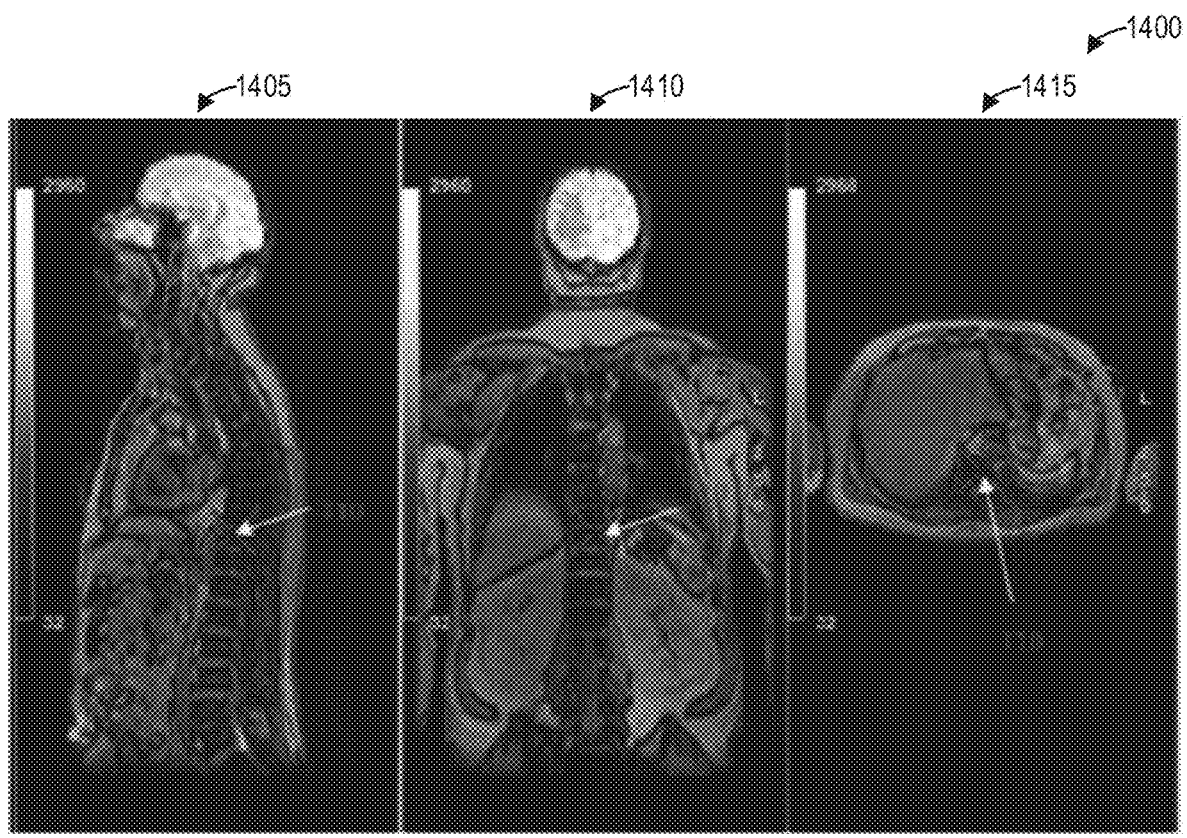
FIG. 14 shows a set of images depicting fusion images in sagittal, coronal, and axial views according to an embodiment.

A method for outputting fused image volumes, such as the method depicted in FIG. 14, includes receiving a request of a specific view of a fused spine image comprising a fusion of the non-functional and the functional MR image volumes, and outputting the requested view of the fused spine image with the automatically generated spine labels and annotations. The anatomical details provided by the non-functional MR images and the details of dynamic activity provided by the functional MR images, along with the automatically-generated labels, may be simultaneously visualized by fusing or overlaying the non-functional and functional MR image volumes, as depicted in FIG. 12. The spine labeling propagated from the non-functional MR image volume to the functional MR image volume may be further propagated from the axial functional view to one or more multiplanar reformatted views, such as axial, coronal, sagittal, and oblique.

Figure 13:
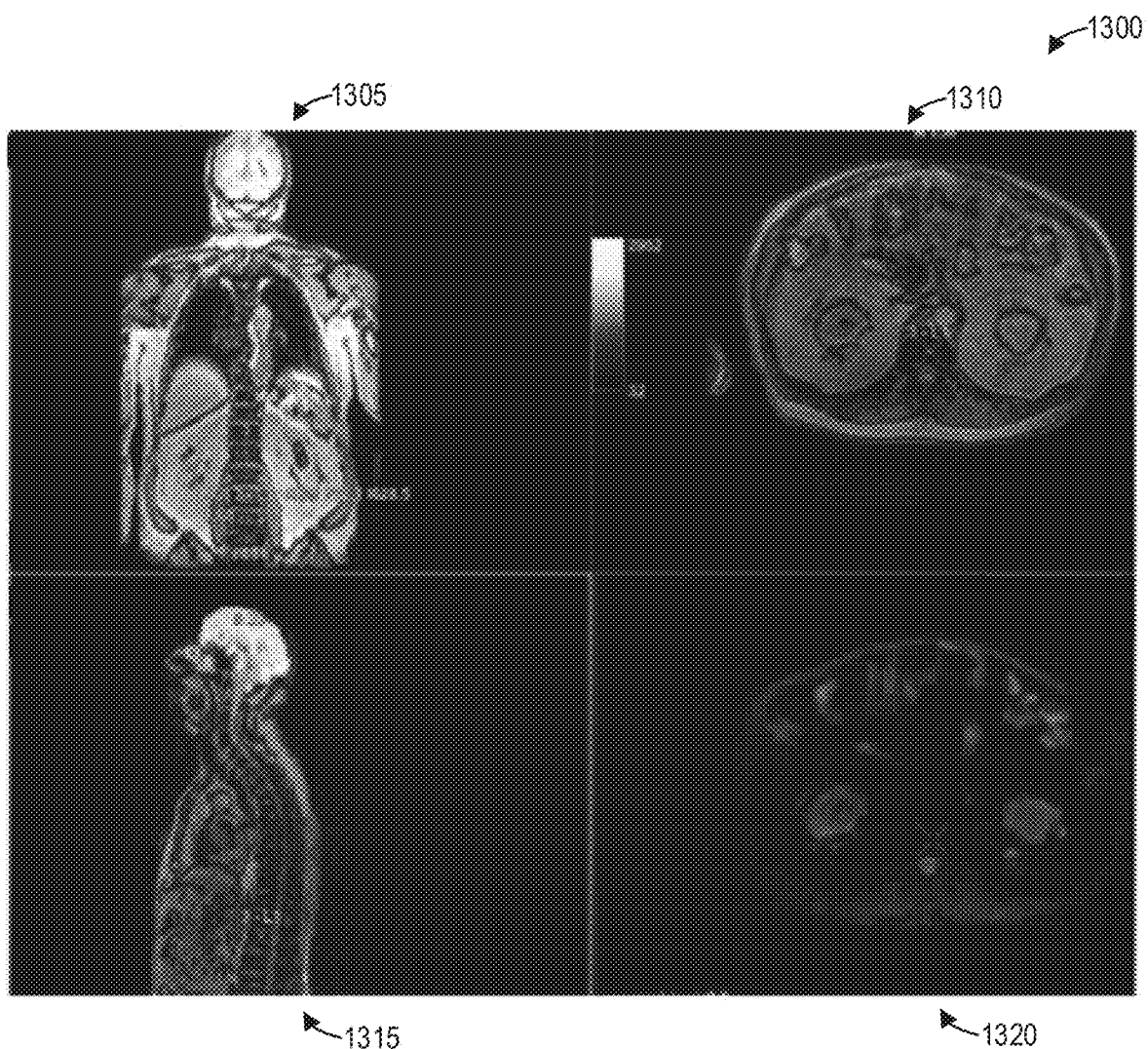
FIG. 13 shows a set of images depicting non-functional MR images and fusion images in different multi-planar reformatted views according to an embodiment.

The multiplanar reformatted views from both functional and non-functional MR image volumes may be fused and displayed as desired by a user. For example, as depicted in FIG. 13, the fusion of non-functional and functional whole-body anatomical data with spine labeling may be displayed in axial and sagittal views alongside un-fused coronal and axial views. As another example, the user may request for displaying the fusion of the non-functional and functional MR data with spine labeling for sagittal, coronal, and/or axial views, as depicted in FIG. 14.

Figure 1:
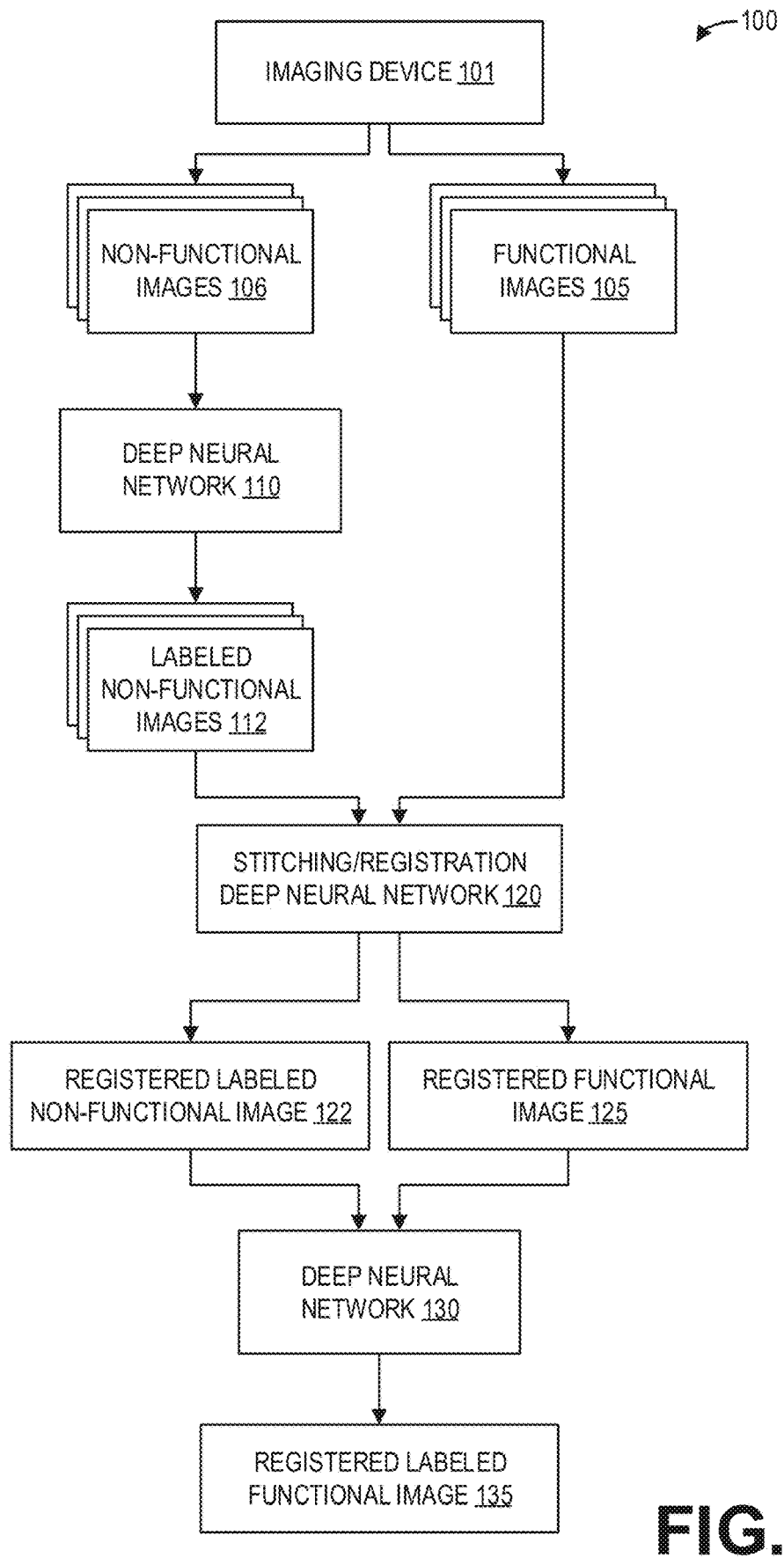
FIG. 1 is a block diagram illustrating an example system for whole-body spine labeling according to an embodiment.

FIG. 1 is a block diagram illustrating an example method 100 for whole-body spine labeling according to an embodiment. An imaging device 101 such as an MRI apparatus scans a subject or patient (not shown) to acquire functional images 105 and non-functional images 106.

The non-functional images 106 are input to a deep neural network 110 trained to automatically segment, label, and annotate the non-functional images 106. As such, labeled non-functional images 112 are output by the deep neural network 110. The labeled non-functional images 112 and the functional images 105 are input to a stitching and registration deep neural network 120, which outputs a registered labeled non-functional image 122 and a registered functional image 125.

The registered labeled non-functional image 122 and the registered functional image 125 are input to a deep neural network 130 for propagating the labels of the registered labeled non-functional image 122 to the registered functional image 125. The deep neural network 130 thus outputs a registered labeled functional image 135.

As an illustrative example, FIG. 2 depicts a neural network 200 having one or more nodes/neurons 202 which, in some embodiments, may be disposed into one or more layers 204, 206, 208, 210, 212, 214, and 216. The neural network 200 may be a deep neural network. As used herein with respect to neurons, the term "layer" refers to a collection of simulated neurons that have inputs and/or outputs connected in similar fashion to other collections of simulated neurons.

Accordingly, as shown in FIG. 2, the neurons 202 may be connected to each other via one or more connections 218 such that data may propagate from an input layer 204, through one or more intermediate layers 206, 208, 210, 212, 214 to an output layer 216.

FIG. 3 shows input and output connections for a neuron in accordance with an exemplary embodiment. As shown in FIG. 3, the connections 218 of an individual neuron 202 may include one or more input connections 302 and one or more output connections 304. Each input connection 302 of a neuron 202 may be an output connection of a preceding neuron, and the output connections 304 of the neuron 202 may be an input connection of one or more subsequent neurons. While FIG. 3 depicts a neuron 202 as having a single output connection 302, it may have multiple output connections that transmit/pass the same value. In embodiment, the neurons 202 may be data constructs, e.g., structures, instantiated class objects, matrices, etc., and the input connections 218 may be received by the neuron 202 as weighted numerical values, e.g., floating point or integer values. For example, as further shown in FIG. 3, input connections X1, X2, and X3 may be weighted via weights W1, W2, and W3, respectively, summed, and sent/transmitted/passed as output connection Y. As will be appreciated, the processing of an individual neuron 202 may be represented, generally, by the equation:

$$Y = f\left(\sum_{i=1}^{n} WiXi\right)$$

where n is the total number of input connections 302 to the neuron 202. In embodiment, the value of Y may be based at least in part on whether the summation of WiXi exceeds a threshold. For example, Y may have a value of zero (0) if the summation of the weighted inputs fails to exceed a desired threshold.

As will be further understood, the input connections 302 of neurons 202 in the input layer 204 may be mapped to the input 201, while the output connections 302 of the neurons 202 in the output layer 216 may be mapped to the output 230. As used herein, "mapping" an input connection 302 to the input 201 refers to the manner by which the input 201 affects/dictates the value of the input connections 302. Similarly, as also used herein, "mapping" an output connection 302 to the output 230 refers to the manner by which the value of the output connections 302 affects the output 230.

Accordingly, in embodiments, the acquired/obtained input 201 is passed/fed to the input layer 204 of the neural network 200 and propagated through the layers 204, 206, 208, 210, 212, 214, and 216 such that mapped output connections 304 of the output layer 216 generates/corresponds to the output 230.

The deep neural network 110 for automatically labeling the non-functional images 106 may comprise a neural network with similar architecture to the deep neural network depicted in FIGS. 2 and 3. Similarly, the deep neural network 130 for propagating the labels of the registered labeled non-functional image 122 to the registered functional image 125 may comprise a neural network with similar architecture to the deep neural network depicted in FIGS. 2 and 3.

Configuration of the deep neural network 110 and the method for automatically segmenting, labeling, and annotating the non-functional images 106 are described in detail in U.S. patent application Ser. No. 15/994,411 filed on May 31, 2018, titled "Methods and Systems for Labeling Whole Spine Image Using Deep Neural Network," which is incorporated herein by reference in its entirety.

The stitching and registration deep neural network 120 of FIG. 1 may also comprise a neural network with similar architecture to the deep neural network depicted in FIGS. 2 and 3, in some examples. In other examples, the deep neural network architecture may be specifically adapted for stitching and registering the functional image volumes and the non-functional image volumes. As an example, FIG. 4 shows a block diagram illustrating an example deep neural network 400 for stitching and registering multi-station or single-station axial spine whole-body image volumes 401 according to an embodiment. The deep neural network 400 performs region-based spine registration with alignment regularization to accurately register the spine in the moving (e.g., functional) volumes. The labeling and anatomical priors of fixed (e.g., non-functional) volumes are fed as an input to the registration network. The alignment regularization is based on Hausdorff distance-based offset correction of the spine discriminators. For the machine learning-based region of interest (ROI) detection, most of the highest ranked spine regions discriminators are located around the spinal vertebrae and the outer body regions between the ribs and the skin. This approach is a non-deterministic algorithm and the resulting probability increases along with the number of input spine region discriminator points and iterations.

The deep neural network 400 simultaneously optimizes and learns region-based spine descriptor spatial transformations, and thus can be directly used to register fixed and moving volumes. Further, the registration of a set of volumes is also a training procedure for the deep neural network 400 so that the trained registration network can be directly adopted to register new fixed and moving volumes by feedforward computation of the learned networks without any optimization.

A workflow for training the neural network 400 includes checking for overlapping spine regions, extracting key region-based spine discriminator points and spine descriptors from the fixed images, extracting key region-based spine discriminator points and spine descriptors from the moving images, performing automatic alignment using geodesics of the key points and/or spine descriptors, matching the key region-based spine discriminator points and spine descriptors using the Hausdorff distance, determining a weighted distance between the fixed (i.e., non-functional volumes) and moving (i.e., functional volumes) spine region-based spine descriptors, generating the training data by collecting near and far spine region descriptors in the moving and fixed images, feeding this data to the neural network, learning the spine descriptor weights, deformation regularization, and spine overlap region threshold.

The network 400 corrects any in-plane rotations that are inherent in both fixed (i.e., non-functional) and moving (i.e., functional) data sets. The network 400 extracts the geodesic-based spine displacement field vector for each of the fixed and moving data sets. The network 400 extracts the mutual information and spatial locations of the spine regions for each of the fixed and moving data sets. The network 400 performs regression to predict the geometrical spine contents for various pulse sequence designs using a deep neural network-based multi-atlas-based spine region geodesic propagation method.

To that end, as depicted in FIG. 4, the functional and non-functional two-dimensional image volumes are fed as input to the network 400. Specifically, from a plurality of multi-station functional and non-functional image volumes 401, a functional image volume and a non-functional image volume are paired prior to input to the network 400. For example, a functional image volume 403 and a non-functional image volume 404 from a first station 402 are paired to form a fixed and moving volume spine region from the first station 405, while a functional image volume 408 and a non-functional image volume 409 from an nth station 407 are paired to form a fixed and moving volume spine region from the nth station 410. Functional image volumes and non-functional image volumes from stations between the first station and the nth station are similarly paired.

The pairs of fixed and moving volume spine regions from the multiple stations are then fed to an input layer 415 of the deep neural network 400. The network 400 then scales and performs convolution of the image volumes at the convolutional layers 417 and 419. The network 400 further performs pooling at the pooling layer 420, with additional convolutions at the convolutional layers 422, 424 prior to down sampling at the down sampling layer 425. Batch normalization is performed at the batch normalization layers 426, 428, 430, and 432, and the batch normalized output is up sampled at up sampling layer 434. The convolved output of convolutional layer 424 and the up sampled output at 434 are combined and convolved at the convolutional layer 435, and then further convolved at convolutional layer 437. The convolved output is up sampled at the up sampling layer 439, and the up sampled output and the convolved output of convolutional layer 419 are combined at the layer 440. Further convolutions are performed at convolutional layers 442 and 444.

The overlap discriminator 450 checks for geometric spine overlaps between the fixed and moving volumes, and classifies the spine displacement vector that has undergone alignment variations within the moving volumes. This step is performed to ensure that the overlap discriminator 450 captures and differentiates variations in the spatial alignments of the spine regions (i.e., between true data distribution obtained from the mutual information and approximated distribution from the regressor 445). The output of the overlap discriminator 450 is then passed through a resample block 452 which resamples spine region locations to improve accuracy of the geodesic spine vector locations in the functional volumes. Further, the discriminator 450 provides the accurate spine region gradient that points in the direction of steepest descent in the loss function landscape.

Output of the regressor 445 is down sampled at down sampling layer 455, followed by a dense and flatten layer 456 and batch normalization layers 457 and 458. Collectively, the down sampling layer 455, dense and flatten layer 456, and batch normalization layers 457, 458 comprise aggregation and spatial transformation layers 459. Aggregation at 459 consists of final geodesic displacement vectors that are corrected for spine regions alone. Additionally, the spatial transformations of each of the displacement vectors of the functional volume are stored in a matrix for mapping between the resampled output of both functional and non-functional volumes. The aggregation and re-sampling takes place simultaneously.

Regularization is a mechanism that is incorporated in the registration network 400 to make suitable modifications to the learning algorithm such that the registration network 400 generalizes region-based spine displacement vectors and spine spatial positions that have undergone alignment variations. This in turn improves the model's performance on the unseen functional and non-functional volumes. The registration network 400 incorporates a dropout-based alignment regularization technique at alignment regularization 460, which compares the output of the aggregator block 445 with resample spin region locations 452 and randomly selects some nodes and removes them along with all their incoming and outgoing connections. This captures more randomness in geometrical misalignments of functional volumes that need further correction. The correction is based on combining the operation output of the aggregated and re-sampled outputs. This allows the registration to normalize the continuity of the spine in subsequent volumes. Further, a similarity metric 462 computes the transformation changes that the moving volumes have undergone during the spine registration.

For the network 400 to perform registration of the functional volumes, the network includes symmetric weights, as well as separate phases for inference and learning. Further, the learning spine displacement vector gradients are local, but are propagated backward 465, layer by layer, from the output units. To that end, the error derivative is transported as a second loss function or loss 464 through the network. To perform the transportation of the loss 464, the derivative of the non-linearities should be known.

Figure 5:
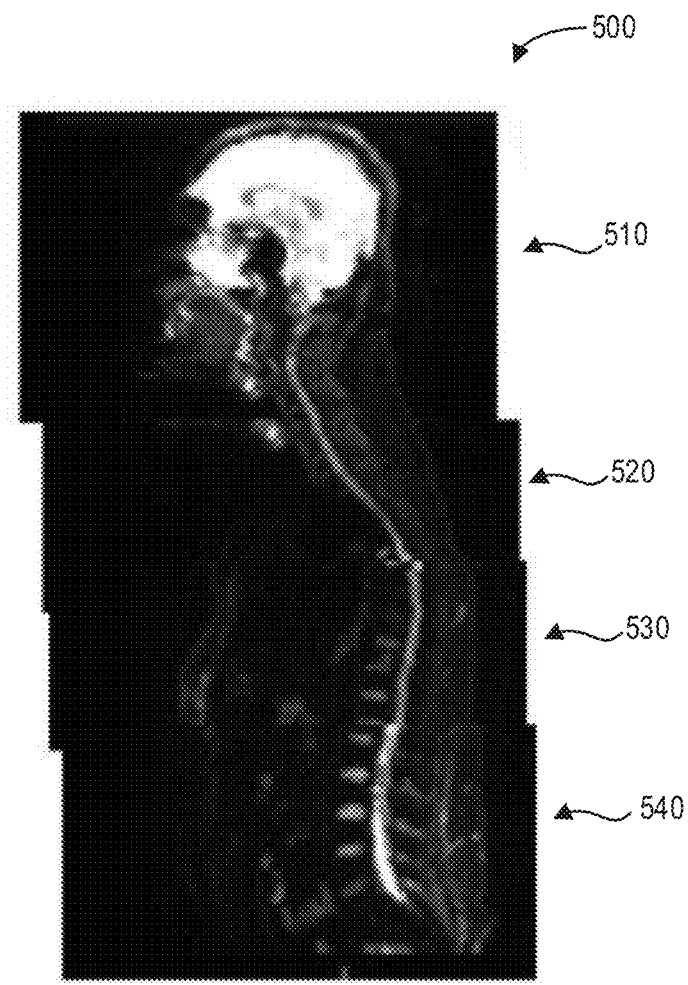
FIG. 5 shows an example stitched and registered multi-station spine image according to an embodiment.

The final output of the deep neural network 400 comprises the moving or functional volumes of all stations 470 stitched and registered accurately according to the fixed or non-functional image volumes. As an illustrative example, FIG. 5 shows an example stitched and registered multi-station spine image volume 500. The stitched and registered multi-station spine image volume 500 comprises a first image volume 510 from a first station, a second image volume 520 from a second station, a third image volume 530 from a third station, and a fourth image volume 540 from a fourth station. The deep neural network 400 automatically registers the image volumes 510, 520, 530, and 540 as described hereinabove and outputs the stitched and registered image volume 500.

It should be understood that the configuration of the deep neural network 400 is shown for illustration and not for limitation. Any appropriate deep neural network with a different configuration (e.g., different number of layers) can be used.

Thus, the systems and deep neural networks described hereinabove enable a systematic technique for automatically labeling a spine in functional image volumes. FIG. 6 shows a high-level flow chart illustrating an example method 600 for labeling functional spine images according to an embodiment. Method 600 is described with regard to the systems and components of FIGS. 1-4, though it should be appreciated that the method 600 may be implemented with other systems and components without departing from the scope of the present disclosure.

Figure 7:
FIG. 7 shows an example whole-body functional MR image volume and a whole-body non-functional MR image volume according to an embodiment.
Figure 7:

Method 600 begins at 605. At 605, method 600 includes acquiring non-functional axial spine image(s). Acquiring non-functional axial spine image(s) comprises performing a non-functional axial scan of a patient at least along the length of a spine of the patient. At 610, method 600 acquires functional axial spine image(s). Acquiring functional axial spine image(s) comprises performing a functional axial scan of the same patient at least along the length of the spine of the patient. In some examples, the non-functional axial scan and the functional axial scan may be performed in succession. However, in other examples, the non-functional axial scan and the functional axial scan may be performed at different times. Thus, in such examples, acquiring the non-functional axial spine image(s) and the functional axial spine image(s) may comprise retrieving, from memory, stored image volumes acquired during a non-functional axial scan and a functional axial scan of the patient. As an illustrative example, FIG. 7 shows a whole-body functional volume 710 and a whole-body non-functional volume 720.

Continuing at 615, method 600 includes segmenting, labeling, and annotating the non-functional axial spine image(s). In particular, method 600 includes automatically segmenting, labeling, and annotating the spine in the non-functional axial spine image(s). To that end, method 600 may input the non-functional axial spine image(s) into a trained neural network to automatically segment, label, and annotate the spine in the non-functional axial spine image(s). As an illustrative example, FIG. 8 shows a non-functional axial image volume 800 with spine labeling 807.

At 620, method 600 includes propagating the labels and segments from the axial view of the non-functional spine image to one or more other multiplanar reformatted views. For example, the labels and segments may be propagated to coronal, sagittal, and/or oblique views. As an illustrative example, FIG. 9 shows a set of images 900 depicting spine labeling 907 propagated from an axial view 910 to various multi-planar reformatted views for a non-functional image volume, including a sagittal view 905, a coronal view 915, and an oblique view 920. In some examples, when multiple views are displayed, correspondence of the labels 907 between views, such as depicted between the coronal view 915 and the oblique view 922, may be visualized.

Referring again to FIG. 6, method 600 continues to 625 after propagating the spine labels to the multiplanar reformatted views. At 625, method 600 includes stitching and registering the non-functional axial spine image(s) and the functional axial spine image(s). The non-functional axial spine image(s) may be stitched and registered in examples wherein the non-functional axial spine image(s) are acquired via multiple stations. However, in some examples, the non-functional axial spine image(s) are acquired via a single station, and so stitching and registration of the non-functional axial spine image is unnecessary. The functional axial spine image(s) may similarly be acquired via a single station or multiple stations. In either example, the functional axial spine image(s) may be stitched and registered according to the non-functional axial spine image(s). In particular, as described hereinabove with regard to FIG. 4, a deep neural network such as the deep neural network 400 may automatically correct geometric misalignments in the spine of the functional image volumes by learning the geometric properties and position of the spine in the non-functional image volumes. Thus, stitching and registering the functional axial spine image(s) may comprise inputting the functional axial spine image(s) along with the non-functional axial spine image(s) into the deep neural network 400.

Continuing at 630, method 600 includes propagating the spine labels and segmented structures of the spine from the registered non-functional axial spine image to the registered functional axial spine image. The propagation of the spine labels and segmented structures of the spine from the registered non-functional axial spine image to the registered functional axial spine image may be performed by a neural network, such as the neural network depicted in FIGS. 2 and 3, trained to receive the registered non-functional and functional axial spine images as well as the spine labels and segmented structures of the non-functional axial spine image, and automatically map or propagate the labels and segments to the functional axial spine image. The geometric corrections applied by the deep neural network 400 to the functional image volumes according to the non-functional image volumes improves the accuracy and ease of propagating the spine labels and segments from the non-functional image volume to the functional image volume. As an illustrative example, FIG. 10 shows a set of images 1000 depicting the propagation of labels 1012 of a spine from a non-functional volume 1010 to a functional volume 1020.

At 635, method 600 includes propagating the labels and segments from the axial view of the registered functional spine image to other multiplanar reformatted views, such as coronal, sagittal, and/or oblique views. The labels and segments may thus be viewed for the functional image volume in any desired view. Continuing at 640, method 600 includes outputting the labeled and segmented registered functional spine image in a requested view. For example, a clinician may request a particular functional view of the spine, and method 600 outputs to a display device or a memory, for example, the requested view with the propagated labels and/or segments. Method 600 then ends.

Figure 11:
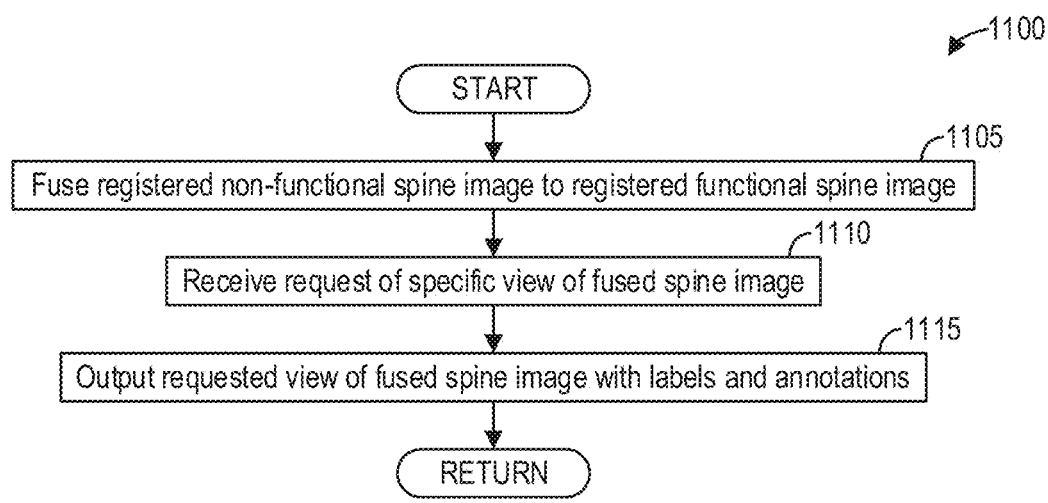
FIG. 11 shows a high-level flow chart illustrating an example method for generating fused images according to an embodiment.

Furthermore, the clinician may desire to view the anatomical details provided by the non-functional image volume along with the dynamic details provided by the functional image volume, in addition to the automatically generated spine labels. FIG. 11 shows a high-level flow chart illustrating an example method 1100 for generating fused images according to an embodiment.

Method 1100 begins at 1105. At 1105, method 1100 includes fusing the registered non-functional spine image to the registered functional spine image. Fusing the registered non-functional spine image to the registered functional spine image may comprise, for example, co-registering and overlaying the non-functional image volume on the functional image volume along with the labels of the non-functional image volume. As an illustrative example, FIG. 12 shows an image 1200 depicting a fusion of non-functional and functional whole body anatomical data with spine labels 1205.

Continuing at 1110, method 1100 includes receiving, from a user such as the clinician, a request of a specific view of the fused spine image. At 1115, method 1100 includes outputting the requested view of the fused spine image with labels and annotations. Method 1100 then ends. Thus, the fusion may be visualized in all the multiplanar reformatted views such as coronal, axial, sagittal, and oblique.

As an illustrative example, FIG. 13 shows a set of images 1300 depicting non-functional images and fusion images in different multiplanar reformatted views, including a coronal view 1305, a fused axial view 1310, a fused sagittal view 1315, and an axial view 1320. Thus, the request of the specific view of the fused spine image may include one or more views of the fused spine image, in addition to one or more views of the non-functional image volume and/or the functional image volume, all according to the desire of the user. As another illustrative example, FIG. 14 shows a set of images 1400 depicting fusion images in a sagittal view 1405, a coronal view 1410, and an axial view 1415.

Thus, the systems and methods provided herein enable the automatic labeling and annotation of the spine in axial whole-body anatomical scans through a deep learning neural network scheme; the automatic propagation, mapping, or transformation of the spine labels/annotations in the axial view to other multiplanar reformatted views such as coronal, oblique, and sagittal; the automatic mapping, propagation, or transformation of the labels from the multiplanar reformatted axial/coronal/sagittal/oblique views of the whole-body non-functional volumes to the corresponding multiplanar reformatted views of the functional volumes of the same patient; the learning of the features of non-functional volumes and automatic correction of any geometrical misalignments or mismatches in the functional volumes; the automatic labeling and annotation of the spine when a user fuses/co-registers/overlays the axial functional whole-body volumes on the non-functional whole-body volume; and the propagation, transformation, or mapping of the labels of the fused spine to other multiplanar fused/co-registered/overlaid reformatted views such as oblique, coronal, and sagittal views.

As an overview, the multi-station or multi-volume axial non-functional anatomical scans are bound into a single whole-body volume. Similarly, the multi-station or multi-volume axial functional anatomical scans are bound into a single whole-body volume. A user may request for automatic segmentation, labeling, and annotation of the spine for the axial non-functional whole-body image volume. An intelligent deep neural network performs the automatic segmentation, labeling, and annotation of the spine. The user may further request the propagation or mapping of the segmented spine labels/contours/annotations to all corresponding multiplanar reformatted views. The user may then visualize the segmented, labeled, annotated spine in all the multiplanar reformatted views such as coronal, axial, sagittal, and oblique.

A technical effect of the disclosure includes the automatic labeling of a spine in a functional image volume. Another technical effect of the disclosure includes the automatic geometrical correction of spinal positions in a functional image volume. Yet another technical effect of the disclosure includes the display of a fused image volume including a non-functional image volume and a functional image volume with automatically-generated labels overlaid thereon.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for magnetic resonance imaging, comprising: automatically labeling a non-functional whole-body image volume of a spine with spine labels, wherein automatically labeling the non-functional whole-body image volume comprises inputting the non-functional whole-body image volume into a first trained neural network, wherein the first trained neural network automatically segments and labels the non-functional whole-body image volume; automatically registering a functional whole-body image volume of the spine to the non-functional whole-body image volume; and propagating the spine labels to the registered functional whole-body image volume.

2. The method of claim 1, wherein automatically registering the functional whole-body image volume comprises inputting the functional whole-body image volume and the non-functional whole-body image volume to a second trained neural network, wherein the second trained neural network automatically corrects geometric mismatch or misalignments in a spine region of the functional whole-body image volume by learning region based geometric properties and positions of the spine in the non-functional whole-body image volume.

3. The method of claim 2, wherein the second trained neural network corrects in-plane rotations that are inherent in both non-functional whole-body image volume and functional whole-body image volume.

4. The method of claim 1, wherein propagating the spine labels to the registered functional whole-body image volume comprises inputting the non-functional whole-body image volume with the spine labels and the registered functional whole-body image volume into a third trained neural network, wherein the third trained neural network maps the spine labels from the non-functional whole-body image volume to the registered functional whole-body image volume.

5. The method of claim 1, further comprising propagating the spine labels from the registered functional whole-body image volume to one or more multiplanar reformatted views of the registered functional whole-body image volume.

6. The method of claim 1, further comprising fusing the non-functional whole-body image volume and the functional whole-body image volume to generate a fused image volume, wherein the fused image volume comprises the non-functional whole-body image volume with the spine labels overlaid on the registered functional whole-body image volume.

7. The method of claim 1, wherein the non-functional whole-body image volume depicts anatomical structure of the spine and the functional whole-body image volume depicts neuronal or diffusivity function of the spine.

8. The method of claim 1, wherein the functional whole-body image volume comprises a diffusion-weighted image volume, PET image volume, or cross-modality image volume.

9. A method, comprising:
geometrically correcting, with a first trained neural network, a position of a spine in the functional whole-body MR image volume of the spine to generate a corrected functional image volume;
propagating, with a second trained neural network, labels of the spine from a non-functional whole-body MR image volume of the spine to the corrected functional image volume; and
displaying a view of the corrected functional image volume with the labels of the spine overlaid on the view;
wherein the method further comprises automatically generating the labels of the spine in the non-functional whole-body MR image volume with a third trained neural network.

10. The method of claim 9, wherein geometrically correcting the position of the spine in the functional whole-body MR image volume comprises inputting the non-functional whole-body MR image volume and the functional whole-body MR image volume into the first trained neural network, wherein the first trained neural network learns a position and orientation of the spine in the non-functional whole-body MR image volume and geometrically corrects the position and/or orientation of the spine in the functional whole-body MR image volume according to the position and/or orientation of the spine in the non-functional whole-body MR image volume.

11. The method of claim 9, wherein the functional whole-body MR image volume comprises a plurality of functional whole-body MR image volumes acquired via multiple imaging stations, wherein geometrically correcting the position or orientation of the spine in the functional whole-body MR image volume comprises geometrically correcting misalignments or mismatches of the spine between the plurality of functional whole-body MR image volumes.

12. The method of claim 11, wherein the corrected functional image volume comprises the plurality of functional whole-body MR image volumes stitched and registered into a single functional whole-body MR image volume with the geometrical corrections.

13. The method of claim 11, wherein the non-functional whole-body MR image volume comprises a plurality of non-functional whole-body MR image volumes acquired via multiple imaging stations, and wherein functional whole-body MR image volumes and non-functional whole-body MR image volumes acquired via corresponding imaging stations are paired as input to the first trained neural network.

14. The method of claim 9, further comprising fusing the non-functional whole-body MR image volume and the functional whole-body MR image volume, and displaying the fusion of the non-functional whole-body MR image volume and the functional whole-body MR image volume with the labels of the spine overlaid thereon.

15. The method of claim 9, wherein the view comprises an axial view, and further comprising propagating the labels from the view of the corrected functional image volume to multiplanar reformatted views including one or more of a sagittal view, a coronal view, and an oblique view.

16. A system for automatically labeling a functional spine image, comprising:
 a first deep neural network configured to register a functional spine image by geometrically correcting the functional spine image according to a position of a spine in a non-functional spine image; and
 a second deep neural network configured to automatically propagate spine labels from the non-functional spine image to the geometrically corrected and registered functional spine image;
 wherein the system further comprises a third deep neural network configured to automatically generate the spine labels for the non-functional spine image.

17. The system of claim 16, wherein the functional spine image comprises a plurality of functional spine images acquired via multiple stations, and wherein the first deep neural network is configured to stitch and register the plurality of functional spine images by geometrically correcting misalignments of the spine between the plurality of functional spine images.

18. The system of claim 16, wherein the spine labels indicate vertebral components of the spine.

* * * * *